United States Patent [19]

Egidio et al.

[11] Patent Number: 5,380,533

[45] Date of Patent: Jan. 10, 1995

[54] GASTRORESISTANT PHARMACEUTICAL FORMULATIONS FOR ORAL ADMINISTRATION CONTAINING BILE ACIDS

[75] Inventors: Marchi Egidio; Tamagnone Gianfranco, both of Casalecchio di Reno; Rotini L. Gabriele, Bologna, all of Italy

[73] Assignee: Alfa Wassermann s.p.A., Alanno Scalo, Italy

[21] Appl. No.: 861,466

[22] Filed: Apr. 1, 1992

[30] Foreign Application Priority Data

Apr. 12, 1991 [IT] Italy .............................. 000113A/91

[51] Int. Cl.$^6$ .............................................. A61K 9/64
[52] U.S. Cl. .................................... 424/456; 424/458; 424/478
[58] Field of Search ........................ 424/456, 458, 478

[56] References Cited

U.S. PATENT DOCUMENTS 3,959,540  5/1976  Leiberich .......................... 424/456
4,263,272  4/1981  Frigerio .............................. 424/486
4,853,230  8/1989  Lovgren ............................. 424/456

Primary Examiner—Thurman K. Page
Assistant Examiner—William E. Benston
Attorney, Agent, or Firm—Bucknam and Archer

[57] ABSTRACT

Pharmaceutical formulations for oral administration coated by an enterosoluble gastroresistant film, preferably selected from gastroresistant granulates, gastroresistant tablets, gastroresistant hard gelatine capsules containing powders or granulates or two or more tablets or oily suspensions, gastroresistant soft gelatine capsules containing oily suspensions and hard gelatine capsules containing gastroresistant granulates or two or more gastroresistant tablets, containing therapeutically effective amounts of bile acids mixed with physiologically compatible basic substances which favor bile acids salification and therefore bile acids absorption in the intestinal tract, process for their preparation and therapeutic use thereof in the treatment of biliary calculoses, biliary dyspepsias, biliary cirrhosis and chronic and cholestatic hepatopathies.

9 Claims, No Drawings

GASTRORESISTANT PHARMACEUTICAL FORMULATIONS FOR ORAL ADMINISTRATION CONTAINING BILE ACIDS

BACKGROUND OF THE INVENTION

The therapeutic activities of some bile acids like, for instance, ursodeoxycholic, chenodeoxycholic, cholic and deoxycholic acids have been well known for some time. At first their use has been addressed to the dissolution of the cholesterol gall-stones, by virtue of their ability of inhibiting the cholesterol synthesis, helping the cholesterol removal through the formation of mixed micelles and inhibiting the cholesterol absorption in the intestine. Subsequently the bile acids have been used to treat biliary dyspepsias, biliary cirrhosis and chronic and cholestatic hepatopathies, as described in Digestive Diseases, 8, (1), 12–22, (1990) by Leuschner U. and Kurz W.

The oral therapy with bile acids until now has been carried out by means of the administration of the acids in form of immediate or delayed release tablets or capsules. All these formulations have the drawback of giving an incomplete absorption, due to scarce bioavailability as clearly shown by Parquet M. et al., European Journal of Clinical Investigation, 15, (4), 171-8, (1985), Igimi H., Corey M. C., J. Lip. Res., 21, 72-90, (1980) and Roda A., Fini A., Hepatology, 4, 72-6, (1984).

This scarce bioavailability is due to the fact that bile acids, particularly ursodeoxycholic acid, dissolve very slowly in the intestine after having crossed unabsorbed and undissolved the stomach.

The water solubility of free bile acids, mainly that of ursodeoxycholic acid, is very low (53 $\mu$M) and, because of its restrained detergence (CMC=14 mM), its solubility is little increased with the increase of the pH and the complete solubilization takes place only at pH 8.47.

Therefore, ursodeoxycholic acid is completely solubilized and absorbed only when the intestinal pH exceeds the value of 8.4, while at lower values of pH a portion of ursodeoxycholic acid is not absorbed and undergoes a biotransformation to lithocholic acid by means of the intestinal bacterial flora.

Therefore it is easily understandable why delayed release formulations containing ursodeoxycholic acid actually can have a lesser bioavailability than that of immediate release formulations in case the delayed release takes place in the intestinal zones where a greater metabolization contemporaneously occurs together with a greater solubilization.

Overcoming the problems of scarce absorption of the immediate or delayed release formulations containing bile acids used at present, is the object of the present invention. This object is obtained by means of enterosoluble gastroresistant pharmaceutical formulations containing bile acids mixed with physiologically compatible basic substances which favour bile acids salification and therefore bile acids absorption in the intestinal tract.

The pharmaceutical formulations must be gastroresistant, because otherwise the strongly acid gastric juices would neutralize the basic substances so that they could not fulfill their function which consists of promoting bile acids solubilization by reacting with them in the intestine to originate the corresponding salts, which are soluble in the intestinal juice and therefore available for the absorption.

This object is achieved by the pharmaceutical formulations object of the present invention as it is clearly shown by biological tests of bioavailability carried out on men, by using a pharmaceutical formulation prepared according to the present invention in comparison with a commercial pharmaceutical formulation of ursodeoxycholic acid.

The experimental results showed a remarkable increase of the bioavailability of the formulation prepared according to the present invention in comparison with the commercial formulation. The average increase of the bioavailability (AUC) is equal to about 40%. Moreover the maximum hematic concentration (C max) reaches average values that are about three times higher and a quicker achievement of the maximum hematic peak (T max) is also noticed: in fact the formulation according to the present invention reached this peak in about 3 and half hours on the average while the commercial formulation reached it in about 4 hours and half.

These experimental data on men clearly show the full achievement of the object of the invention and therefore the pharmaceutical formulations object of the present invention are perfectly suitable for the therapeutic uses of the bile acids, mainly for the treatment of biliary calculoses, biliary dyspepsias, biliary cirrhosis and chronic and cholestatic hepatopathies.

DETAILED DESCRIPTION OF THE INVENTION

Pharmaceutical formulations for oral use coated by an enterosoluble gastroresistant film containing therapeutically effective amounts of bile acids mixed with physiologically compatible basic substances, which favour bile acids salification and therefore bile acids absorption in the intestinal tract, are the object of the present invention.

The process for preparing said pharmaceutical formulations and their therapeutic use in the treatment of biliary calculoses, biliary dyspepsias, biliary cirrhosis and chronic and cholestatic hepatopathies are further objects of the present invention.

Every kind of gastroresistant pharmaceutical formulations for oral use suitable for the fulfillment of the present invention. Gastroresistant granulates, gastroresistant tablets, gastroresistant hard gelatine capsules containing powders or granulates or two or more tablets or oily suspensions, gastroresistant soft gelatine capsules containing oily suspensions and hard gelatine capsules containing gastroresistant granulates or two or more gastroresistant tablets, containing a therapeutically effective amount of bile acids mixed with physiologically compatible basic subtances, are the preferred forms.

The distinctive feature of these pharmaceutical formulations resides in that they are coated by an enterosoluble gastroresistant film which allows the mixture of bile acids and physiologically compatible basic substances to cross the gastric juices unaltered and to be dissolved in the intestine where the absorption takes place. These pharmaceutical formulations contain an amount of bile acids comprised between 50 and 750 mg and can be administered one or more times a day depending on the dosages and the individual therapeutic needs.

All the bile acids endowed with therapeutic activity can be advantageously used in the fulfillment of the present invention.

The cholic, deoxycholic, chenodeoxycholic, iocholic, iodeoxycholic and ursodeoxycholic acids are preferred in the realization of the present invention.

There are many basic substances which can be advantageously used in the fulfillment of the present invention. The limit of their use is essentially due to two factors: one, of biological kind, consists in that these basic substances must be physiologically compatible with human organism; the other, of chemical nature, depends on that the said substances must have a sufficient basic character in order to allow bile acids salification in the intestinal juice.

The basic substances preferably used in the realization of the present invention can be divided into two main groups: organic substances with basic character and salts of organic or inorganic acids with a lower degree of acidity than bile acids and thus able to salify the bile acids themselves.

Aliphatic amines like diethanolamine, triethanolamine and tromethamine, heterocyclic bases like piperazine, N-methylpiperidine and 1-(2-hydroxyethyl)pyrrolidine, basic aminoacids like L-arginine, L-lysine and L-ornithine, quaternary ammonium derivatives like choline and aminosugars like glucosamine, D-glucamine and N-methyl-D-glucamine belong to the first group.

Sodium bicarbonate, disodium phosphate, sodium maleate, potassium bicarbonate and choline bicarbonate belong to the second category.

The amount of basic substance which is added to bile acid can vary within wide limits and it can be whether lesser or equal or larger than the stoichiometric amount required to salify all the bile acid.

In the first case it is preferred to salify only partly the bile acid and to leave a non-salified part: in this way a controlled absorption can be achieved which consists of rapid absorption of the salified bile acid and slow absorption of the non-salified part.

In the second case a quick absorption is obtained because of complete salification of the bile acid with the basic substance in the intestinal juice.

The amount of physiologically compatible basic substance preferably used in the present invention is comprised between 0.5 and 3 molar equivalents for each bile acid molar equivalent to be salified.

All the enterosoluble gastroresistant pharmaceutical formulations for oral use can be advantageously used in the realization of the present invention. The preferred formulations are the gastroresistant tablets, the gastroresistant, both hard and soft, capsules and the capsules containing two or more gastroresistant tablets. In this last case the gastroresistant film can be different for each kind of tablet so that each tablet can be solubilized in a different tract of the intestine in order to greatly aid the absorption of the drug.

Gastroresistant coatings that can be solubilized at pH values respectively higher than 5, 6 and 7, so that the solubilization takes place in the desired manner, were selected for carrying out the present invention.

The non-coated pharmaceutical forms are prepared according to known methods by using normal excipients, for instance binding agents lake polyvinylpyrrolidone, carboxymethylcellulose, microgranular cellulose, lactose, saccharose or mannitol, disintegrating agents like reticulated polyvinylpyrrolidone, starches, sodium starch glycolate or alginates, lubricating agents like talc, magnesium stearate or stearic acid.

The non-coated pharmaceutical forms obtained according to known methods are transformed into the enterosoluble gastroresistant pharmaceutical formulations object of the present invention by means of a double coating.

The first coating, which is not protective, is carried out by using hydroxypropylmethylcellulose, polyethylene glycol 6000, titanium dioxide, talc and, optionally, pharmaceutically acceptable dyestuffs like, for instance, the iron oxides. This coating creates a film which acts as support for obtaining an optimal setting of the subsequent enterosoluble gastroresistant protective film on the pharmaceutical form. Many coating substances can be advantageously used to obtain an enterosoluble gastroresistant coating. Cellulose acetate, the copolymers of the methacrylic acid and of the methacrylic esters in different ratios, commercially known under the trademark EUDRAGIT , mainly EUDRAGIT L and EUDRAGIT S, polyvinylacetophthalate and hydroxypropylmethylcellulose phthalate.

Plasticizers, in an amount comprised between 5% and 15% in weight with respect to the amount of coating agent, are added for granting optimal flexibility and elasticity to the gastroresistant film.

Diethylphthalate, dibutylphthalate, triacetin, polyethylene glycols and acetylated monoglycerides are the plasticizers preferred in the realization of the present invention.

The process for preparing the pharmaceutical formulations object of the present invention comprises making the various pharmaceutical forms for oral use not coated by the protective film according to known methods. For instance the tablets are prepared by dry granulating the bile acid, by mixing it with the basic substance and normal excipients like, for instance, reticulated polyvinylpyrrolidone, microgranular cellulose, magnesium stearate and talc and tabletting the resulting mixture.

The hard gelatine capsules can be filled either with a powder made by the sole mixture of the active principle and the basic substance or by the above mentioned mixture together with one or more excipients, either with a granulate containing the active principle and the basic substance alone or together with one or more excipients, or with a suspension of the active principle together with the basic substance in a suitable dispersing agent.

Afterwards the capsules are sealed, for instance, with an aqueous or hydroalcoholic solution of gelatine.

The soft gelatine capsules can be filled with a suspension of the active principle and of the basic substance in a suitable dispersing agent and then they are sealed.

The tablets or the capsules, so obtained by means of known methods, are then submitted to the gastroprotection. A first, non-protective, coating, useful as support for obtaining an optimal setting of the protective enterosoluble gastroresistant film on the pharmaceutical form, is carried out before executing the coating by means of the enterosoluble gastroresistant film.

This non-protective coating is carried out by sprying on the pharmaceutical forms in coating pan a suspension made by hydroxypropylmethylcellulose, polyethylene glycol 6000, titanium dioxide, talc and, optionally, pharmaceutically acceptable dyestuffs like, for instance, the iron oxides, in a 22:1 mixture of ethyl alcohol and water. The weight of this first film is comprised between 1% and 5% of the weight of the non-coated pharmaceutical form.

The application of the enterosoluble gastroresistant film is carried out by solubilizing one or more coating substances together with one or more plasticizers in a solvent selected from methyl, ethyl or isopropyl alcohol, acetone or mixtures thereof with water and spraying this solution in coating pan on the pharmaceutical formulations previoulsy coated by means of the non-protective coating, in such an amount that the weight of the enterosoluble gastroresistant film is comprised between 2% and 10% with respect to the weight of the non-coated pharmaceutical form.

The so obtained enterosoluble gastroresistant pharmaceutical formulations release, directly in the intestinal fluid, the mixture formed by the bile acid and the physiologically compatible basic substance which favours in situ salification and therefore absorption of the bile acid in the intestinal tract.

In this way, the bile acid can be immediately solubilized and it can be absorbed in a faster and more complete way by the intestinal tract as it is clearly shown by the experimental results of a pharmacokinetic test carried out on man.

A tablet, coming from a commercial pharmaceutical formulation containing 450 mg of ursodeoxycholic acid, was administered to each of 9 healthy subjects having a normal body weight, fasting for 8 hours.

One week later the same persons were given, under the same circumstances, a tablet containing 450 mg of ursodeoxycholic acid and prepared according to the method described in Example 1.

The hematic levels of ursodeoxycholic acid were evaluated for a period of time of 8 hours starting from the administration of the drug. They were evaluated by means of an immunoenzymatic method that uses specific antibodies for the free ursodeoxycholic acid prepared in New Zealand rabbits as described in articles of Roda A. et al. in Talanta, 31, 895, (1984) and in Analytical Biochemistry, 156, (2), 267–73, (1986).

The experimental results of the absorption during 8 hours, expressed as the area contained under the hematic curve (AUC). calculated as $\mu$moles/$\frac{1}{8}$h, as the maximum hematic concentration that has been obtained (C max), expressed as $\mu$moles/1, and as the time, expressed as hours, in which said maximum concentration has been obtained after the administration of the drug (T max), are reported in table 1.

cal formulation. Moreover the maximum hematic concentrations (C max) reached after the administration of the formulation described in example 1 are on the average three times higher than the maximum hematic concentrations reached after the administration of the commercial formulation. Lastly, also the speed of absorption is higher, because the reaching of the maximum hematic peak (T max) occurs, on the average, after about 3 and half hours after the treatment with the formulation according to example 1, i.e. about 1 hour before this reaching occurs with the commercial formulation of ursodeoxycholic acid.

Therefore the object of the present invention of producing oral pharmaceutical formulations containing a bile acid as the active principle and endowed with a better bioavailability in comparison with the pharmaceutical forms at present used, has been fully achieved.

These oral gastroresistant pharmaceutical forms contain therapeutically effective amounts of bile acids, preferably comprised between 50 and 750 mg, and can be administered one or more times a day, depending on the dosages and the individual therapeutic needs, in the treatment of biliary calculoses, biliary dyspepsias, biliary cirrhosis and chronic and cholestatic hepatopathies.

The examples reported have to be considered only as a further illustration and not as a limitation of the invention.

EXAMPLE 1

Gastroresistant Tablets Containing Ursodeoxycholic Acid and Sodium Bicarbonate

| Composition of each tablet | |
|---|---|
| Ursodeoxycholic acid | 450 mg |
| Sodium bicarbonate | 100 mg |
| Reticulated polyvinylpyrrolidone | 21 mg |
| Microgranular cellulose | 210 mg |
| Magnesium stearate | 12 mg |
| Talc | 6 mg |
| Hydroxypropylmethylcellulose | 14 mg |
| Polyethylene glycol 6000 | 0.4 mg |
| Titanium dioxide | 3.2 mg |
| Talc | 3.2 mg |
| Hydroxypropylmethylcellulose phthalate | 38.4 mg |
| Acetylated monoglycerides | 3.8 mg |

The ursodeoxycholic acid is dry compacted and

TABLE 1

| | ABSORPTION TEST IN MAN | | | | | |
|---|---|---|---|---|---|---|
| | Ursodeoxycholic acid and sodium bicarbonate according to Example 1 | | | Commercial formuluation of ursodeoxycholic acid | | |
| Person | AUC (umoles/1/8 h) | Cmax (umoles/1) | Tmax (h) | AUC ($\mu$moles/1/8 h) | Cmax ($\mu$moles/1) | Tmax (h) |
| 1 | 45.4 | 31 | 3.1 | 38.2 | 8 | 4 |
| 2 | 39.2 | 25 | 2.4 | 27.6 | 6 | 4.2 |
| 3 | 42.5 | 33 | 4.2 | 20.5 | 4 | 3.9 |
| 4 | 31.3 | 17 | 3.4 | 23.2 | 5 | 4.5 |
| 5 | 49.2 | 21 | 2.7 | 32.4 | 12 | 5.2 |
| 6 | 51.5 | 23 | 3 | 30.4 | 7 | 3.8 |
| 7 | 43.7 | 19 | 3.5 | 29.6 | 6 | 4.5 |
| 8 | 34.9 | 31 | 4 | 38.6 | 9 | 4.6 |
| 9 | 31.8 | 22 | 3.6 | 36.1 | 10 | 5.5 |
| $\bar{x} \pm$ s.d. | 41.06 $\pm$ 6.88 | 24.67 $\pm$ 5.42 | 3.32 $\pm$ 0.55 | 30.73 $\pm$ 5.98 | 7.44 $\pm$ 2.41 | 4.47 $\pm$ 0.55 |

The experimental data reported in table 1 show that the absorption in man (expressed as AUC), by administering the same amount of the active principle, i.e. of ursodeoxycholic acid, increases of a value of about 40% for the pharmaceutical formulation according to example 1 in comparison with the commercial pharmaceutical formulation.

granulated on a 0.8 mm sieve. The granulate is mixed for 15 minutes with sodium bicarbonate, reticulated polyvinylpyrrolidone, microgranular cellulose, magnesium stearate and talc and then the mixture is tabletted.

The tablets are coated in coating pan first with a dispersion of hydroxypropylmethylcellulose, polyethylene glycol 6000, titanium dioxide and talc in a 22:1 mixture of ethyl alcohol and water and then with a solution of hydroxypropylmethylcellulose phthalate and acetylated monoglycerides in a 89:11 mixture of ethyl alcohol and water.

EXAMPLE 2

Gastroresistant Tablets Containing Chenodeoxycholic Acid and Sodium Bicarbonate

| Composition of each tablet | |
|---|---|
| Chenodeoxycholic acid | 300 mg |
| Sodium bicarbonate | 70 mg |
| Reticulated polyvinylpyrrolidone | 14 mg |
| Microgranular cellulose | 140 mg |
| Magnesium stearate | 8 mg |
| Talc | 4 mg |
| Hydroxypropylmethylcellulose | 10 mg |
| Polyethylene glycol 6000 | 0.3 mg |
| Titanium dioxide | 2.1 mg |
| Talc | 2.1 mg |
| Hydroxypropylmethylcellulose phthalate | 25.2 mg |
| Acetylated monoglycerides | 2.5 mg |

The tablets are prepared and coated according to the manner described in example 1.

EXAMPLE 3

Gastroresistant Tablets Containing Ursodeoxycholic Acid and Disodium Phosphate

| Composition of each tablet | |
|---|---|
| Ursodeoxycholic acid | 300 mg |
| Disodium phosphate | 120 mg |
| Reticulated polyvinylpyrrolidone | 21 mg |
| Microgranular cellulose | 210 mg |
| Magnesium stearate | 12 mg |
| Talc | 6 mg |
| Hydroxypropylmethylcellulose | 14 mg |
| Polyethylene glycol 6000 | 0.4 mg |
| Titanium dioxide | 3.2 mg |
| Talc | 3.2 mg |
| Hydroxypropylmethylcellulose phthalate | 38.4 mg |
| Acetylated monoglycerides | 3.8 mg |

The tablets are prepared and coated according to the manner described in example 1.

EXAMPLE 4

Gastroresistant Tablets Containing Chenodeoxycholic Acid and Disodium Phosphate

| Composition of each tablet | |
|---|---|
| Chenodeoxycholic acid | 150 mg |
| Disodium phosphate | 60 mg |
| Reticulated polyvinylpyrrolidone | 21 mg |
| Microgranular cellulose | 210 mg |
| Magnesium stearate | 12 mg |
| Talc | 6 mg |
| Hydroxypropylmethylcellulose | 14 mg |
| Polyethylene glycol 6000 | 0.4 mg |
| Titanium dioxide | 3.2 mg |
| Talc | 3.2 mg |
| Hydroxypropylmethylcellulose phthalate | 32 mg |
| Acetylated monoglycerides | 3.2 mg |

The tablets are prepared and coated according to the manner described in example 1.

EXAMPLE 5

Gastroresistant Tablets Containing Ursodeoxycholic Acid and Sodium Maleate

| Composition of each tablet | |
|---|---|
| Ursodeoxycholic acid | 150 mg |
| Sodium maleate | 62.5 mg |
| Reticulated polyvinylpyrrolidone | 7 mg |
| Microgranular cellulose | 70 mg |
| Magnesium stearate | 4 mg |
| Talc | 2 mg |
| Hydroxypropylmethylcellulose | 4.7 mg |
| Polyethylene glycol 6000 | 0.13 mg |
| Titanium dioxide | 1.1 mg |
| Talc | 1.1 mg |
| Hydroxypropylmethylcellulose phthalate | 12.8 mg |
| Acetylated monoglycerides | 1.3 mg |

The tablets are prepared and coated according to the manner described in example 1.

EXAMPLE 6

Gastroresistant Hard Gelatine Capsules Containing Ursodeoxycholic Acid and Sodium Maleate

| Composition of each capsule | |
|---|---|
| Ursodeoxycholic acid | 300 mg |
| Sodium maleate | 125 mg |
| Reticulated polyvinylpyrrolidone | 15 mg |
| Maize starch | 10 mg |
| Magnesium stearate | 10 mg |
| Talc | 7 mg |
| Hydroxypropylmethylcellulose | 5 mg |
| Polyethylene glycol 6000 | 0.2 mg |
| Titanium dioxide | 1.2 mg |
| Talc | 1.2 mg |
| Eudragit ® L | 20.7 mg |
| Dibutylphthalate | 2 mg |

The ursodeoxycholic acid is mixed with sodium maleate and the maize starch for 30 minutes and then the mixture is dry compacted and granulated on a 1 mm sieve. The granulate is mixed for 15 minutes with reticulated polyvinylpyrrolidone, magnesium stearate and talc and the mixture is shared in hard gelatine capsules that are sealed with a 31% (w/v) aqueous solution of gelatine and then are coated in coating pan first with a dispersion of hydroxypropylmethylcellulose, polyethylene glycol 6000, titanium dioxide and talc in a 22:1 mixture of ethyl alcohol and water and then with a solution of Eudragit L and dibutylphthalate in isopropyl alcohol.

EXAMPLE 7

Gastroresistant Soft Gelatine Capsules Containing Ursodeoxycholic Acid and L-arginine

| Composition of each capsule | |
|---|---|
| Ursodeoxycholic acid | 225 mg |
| L-arginine | 75 mg |
| Precipitated silica | 3 mg |
| Caprilo-capric glycerides | 450 mg |
| Hydroxypropylmethylcellulose | 10.5 mg |
| Polyethylene glycol 6000 | 0.6 mg |
| Titanium dioxide | 2.4 mg |
| Talc | 2.4 mg |
| Hydroxypropylmethylcellulose phthalate | 32 mg |
| Acetylated monoglycerides | 3.2 mg |

A mixture of ursodeoxycholic acid, L-arginine, precipitated silica and caprilo-capric glycerides is homogenized in a cylinder mill and then is shared in type 11 oval soft gelatine capsules. These capsules are first coated in coating pan with a first film made by a suspension of hydroxypropylmethylcellulose, polyethylene glycol 6000, titanium dioxide and talc in a 22:1 mixture of 95% ethyl alcohol and water. Subsequently an enterosoluble gastroresistant coating is carried out by sprying in coating pan a solution of hydroxypropylmethylcellulose phthalate and acetylated monoglycerides in a 80:1 mixture of ethyl alcohol and water on the capsules coated with the first film.

EXAMPLE 8

Hard Gelatine Capsules Containing Three Gastroresistant Tablets Containing Ursodeoxycholic Acid and Disodium Phosphate

| Composition of each non-protected tablet | |
|---|---|
| Ursodeoxycholic acid | 150 mg |
| Disodium phosphate | 60 mg |
| Reticulated polyvinylpyrrolidone | 7 mg |
| Microgranular cellulose | 55 mg |
| Magnesium stearate | 4 mg |
| Talc | 2 mg |

The ursodeoxycholic acid is dry compacted and granulated on a 0.8 mm sieve. The granulate is mixed for 15 minutes with disodium phosphate, reticulated polyvinylpyrrolidone, microgranular cellulose, magnesium stearate and talc and then the mixture is tabletted. The obtained tablets are shared in three identical portions, each of which is submitted to a different kind of gastroprotection indicated by the letters A, B and C.

| Coating of each type A tablet | |
|---|---|
| Hydroxypropylmethylcellulose | 6 mg |
| Polyethylene glycol 6000 | 0.2 mg |
| Titanium dioxide | 1.4 mg |
| Talc | 1.4 mg |
| Hydroxypropylmethylcellulose phthalate | 13 mg |
| Acetylated monoglycerides | 1.3 mg |

The tablets are coated in coating pan first with a dispersion of hydroxypropylmethylcellulose, polyethylene glycol 6000, titanium dioxide and talc in a 22:1 mixture of ethyl alcohol and water and then with a solution of hydroxypropylmethylcellulose phthalate and acetylated monoglycerides in a 89:11 mixture of ethyl alcohol and water.

The gastroprotected tablets of type A are solubilized at a pH value higher than 5.

| Coating of each type B tablet | |
|---|---|
| Hydroxypropylmethylcellulose | 6 mg |
| Polyethylene glycol 6000 | 0.2 mg |
| Titanium dioxide | 1.4 mg |
| Talc | 1.4 mg |
| Yellow iron oxide | 0.6 mg |
| Eudragit ® L | 13 mg |
| Dibutylphthalate | 1.3 mg |

The tablets are coated in coating pan first with a dispersion of hydroxypropylmethylcellulose, polyethylene glycol 6000, titanium dioxide, talc and yellow iron oxide in a 22:1 mixture of ethyl alcohol and water and then with a solution of Eudragit L and dibutylphthalate isopropyl alcohol. The gastroprotected tablets of type B are solubilized at a pH value higher than 6.

| Coating of each type C tablet | |
|---|---|
| Hydroxypropylmethylcellulose | 6 mg |
| Polyethylene glycol 6000 | 0.2 mg |
| Titanium dioxide | 1.4 mg |
| Talc | 1.4 mg |
| Red iron oxide | 0.6 mg |
| Eudragit ® s | 13 mg |
| Dibutylphthalate | 1.3 mg |

The tablets are coated in coating pan first with a dispersion of hydroxypropylmethylcellulose, polyethylene glycol 6000, titanium dioxide, talc and red iron oxide in a 22:1 mixture of ethyl alcohol and water and then with a solution of Eudragit S and dibutylphthalate in isopropyl alcohol. The gastroprotected tablets of type C are solubilized at a pH value higher than 7.

The hard gelatine capsules are then filled with three gastroresistant tablets, one of each type A, B and C.

EXAMPLE 9

Hard Gelatine Capsules Containing Two Gastroresistant Tablets of Chenodeoxycholic Acid and Disodium Phosphate

| Composition of each non-protected tablet | |
|---|---|
| Chenodeoxycholic acid | 150 mg |
| Disodium phosphate | 60 mg |
| Reticulated polyvinylpyrrolidone | 7 mg |
| Microgranular cellulose | 55 mg |
| Magnesium stearate | 4 mg |
| Talc | 2 mg |

The chenodeoxycholic acid is dry compacted and granulated on a 0.8 mm sieve. The granulate is mixed for minutes with disodium phosphate, reticulated polyvinylpyrrolidone, microgranular cellulose, magnesium stearate and talc and then the mixture is tabletted. The obtained tablets are divided in two identical portions, each of which is submitted to a different kind of gastroprotection indicated by the letters A and B.

| Coating of each type A tablet | |
|---|---|
| Hydroxypropylmethylcellulose | 6 mg |
| Polyethylene glycol 6000 | 0.2 mg |
| Titanium dioxide | 1.4 mg |
| Talc | 1.4 mg |
| Hydroxypropylmethylcellulose phthalate | 13 mg |
| Acetylated monoglycerides | 1.3 mg |

The tablets are coated as described for the type A tablets of example 8.

| Coating of each type B tablet | |
|---|---|
| Hydroxypropylmethylcellulose | 6 mg |
| Polyethylene glycol 6000 | 0.2 mg |
| Titanium dioxide | 1.4 mg |
| Talc | 1.4 mg |
| Red iron oxide | 0.6 mg |
| Eudragit ® S | 13 mg |
| Dibutylphthalate | 1.3 mg |

The tablets are coated as described for the type C tablets of example 8.

The hard gelatine capsules are then filled with a type A tablet and with a type B tablet.

EXAMPLE 10

Hard Gelatine Capsules Containing Two Gastroresistant Tablets Containing Ursodeoxycholic Acid and Piperazine The capsules are prepared as described in example 9 by using for each tablet 75 mg of ursodeoxycholic acid, 45 mg of hexahydrate piperazine and an amount of excipients and coating agents equal to half of that described in example 9.

EXAMPLE 11

Hard Gelatine Capsules Containing Two Gastroresistant Tablets Containing Ursodeoxycholic Acid and N-methyl-D-glucamine The capsules are prepared as described in example 9 by using for each tablet 75 mg of ursodeoxycholic acid, 40 mg of N-methyl-D-glucamine and an amount of excipients and coating agents equal to half of that described in example 9.

We claim:

1. A pharmaceutical composition for oral use in the form of at least one tablet or a capsule, comprising 50–750 mgs of a bile acid mixed with 0.5–3 molar equivalents of a physiologically compatible basic substance, said at least one tablet or capsule being first coated with a non-protective film in the amount of 1–5% by weight said non-protective film comprising hydroxypropylmethyl cellulose, polyethylene glycol 6000, titanium dioxide and talc and then coated with an enterosoluble gastroresistant coating in the amount of 2–10% by weight, said composition being completely insoluble at pH lower than 5.

2. The composition according to claim 1 wherein said non-protective film additionally comprises a pharmaceutically acceptable dyestuff.

3. The composition according to claim 1 wherein said bile acid is a member selected from the group consisting of cholic, deoxycholic, chenodeoxycholic, iocholic, iodeoxycholic and ursodeoxycholic acid.

4. The composition according to claim 1 wherein said basic substance is a member selected from the group consisting of diethanolamine, triethanolamine, tromethamine, N-methylpiperidine, piperazine, 1-(2-hydroxyethyl)pyrrolidine, L-arginine, L-lysine, L-ornithine, D-glucamine, N-methyl-D-glucamine, glucosamine, choline, sodium bicarbonate, disodium phosphate, sodium maleate, potassium bicarbonate and choline bicarbonate.

5. The composition according to claim 3 wherein said gastroresistant coating comprises at member selected from the group consisting of cellulose acetate, copolymers of methacrylic acid and of methacrylic esters in different ratios, polyvinylacetophthalate and hydroxypropylmethycellulose phthalate and a plasticizer which is a member selected from the group consisting of diethylphthalate, dibutylphthalate, triacetin, polyethylene glycols and acetylated monoglycerides.

6. The composition according to claim 1, which contains two tablets, said tablets being coated with the same non-protective film, one of said tablets being coated with a gastroresistant enterosoluble coating which is soluble at a pH higher than 5, the other tablet being coated with a gastroresistant enterosoluble coating which is solubilized at pH higher than 7.

7. The composition according to claim 1 which contains three tablets, said tablets being coated with the same non-protective film, the first tablet being coated with a gastroresistant enterosoluble coating which is soluble at pH higher than 5, the second tablet being coated with a gastroresistant enterosoluble film which is soluble at pH higher than 6, the third tablet being soluble at a pH higher than 7.

8. The method of treatment of a living subject affected by biliary calculoses, biliary dyspepsias, biliary cirrhosis, chronic and cholestatic hepatopaty, which consists of orally administering to said subject a composition consisting of a tablet or capsule containing 50–750 mgs of bile acid and 0.5–3 molar equivalents of a physiologically compatible basic substance, said tablet or capsule being coated with a non-protective coating and a gastroresistant enterosoluble coating on the exterior thereof whereby said composition is insoluble in the stomach of said living subject but is soluble at pH higher than 5.

9. A pharmaceutical composition for oral use in the form of at least one tablet or a capsule, comprising 50–750 mgs of a bile acid mixed with at least the stoichiometric amount of a physiologically compatible basic substance, said at least one tablet or capsule being first coated with a non-protective film in the amount of 1–5% by weight with respect to said non-coated portion, said non-protective film comprising hydroxypropylmethyl cellulose, polyethylene glycol 6000, titanium dioxide and talc and then coated with an enterosoluble gastroresistant coating in the amount of 2–10% by weight, said composition being insoluble at pH lower than 5, but being immediately soluble at pH of 8.4.

* * * * *